United States Patent
Saitou et al.

(10) Patent No.: US 12,036,428 B2
(45) Date of Patent: Jul. 16, 2024

(54) POSITIVE PRESSURE EXHALE VALVE FOR A BREATHING APPARATUS

(71) Applicant: SHIGEMATSU WORKS CO., LTD., Tokyo (JP)

(72) Inventors: Wataru Saitou, Saitama (JP); Kenichi Ono, Saitama (JP); Hiroyuki Ide, Saitama (JP)

(73) Assignee: SHIGEMATSU WORKS CO., LTD., Tokyo (JP)

( * ) Notice: Subject to any disclaimer, the term of this patent is extended or adjusted under 35 U.S.C. 154(b) by 987 days.

(21) Appl. No.: 16/490,997

(22) PCT Filed: Mar. 15, 2018

(86) PCT No.: PCT/JP2018/010096
§ 371 (c)(1),
(2) Date: Sep. 4, 2019

(87) PCT Pub. No.: WO2018/193761
PCT Pub. Date: Oct. 25, 2018

(65) Prior Publication Data
US 2020/0038696 A1    Feb. 6, 2020

(30) Foreign Application Priority Data

Apr. 18, 2017 (JP) .................................. 2017-081785

(51) Int. Cl.
*A62B 18/10* (2006.01)
*A62B 18/02* (2006.01)
*A61M 16/20* (2006.01)

(52) U.S. Cl.
CPC .............. *A62B 18/10* (2013.01); *A62B 18/02* (2013.01); *A61M 16/208* (2013.01)

(58) Field of Classification Search
CPC ..................................................... A62B 18/10
See application file for complete search history.

(56) References Cited

U.S. PATENT DOCUMENTS

| | | | | |
|---|---|---|---|---|
| 2,299,079 A | * | 10/1942 | Davis ...................... | F16K 17/18 |
| | | | | 137/514.3 |
| 2,629,375 A | | 2/1953 | Holmes | |
| 4,190,045 A | * | 2/1980 | Bartels .................. | A61M 16/20 |
| | | | | 128/205.24 |

(Continued)

FOREIGN PATENT DOCUMENTS

| | | |
|---|---|---|
| JP | 61-160224 U | 10/1986 |
| JP | 3-69373 U | 7/1991 |

(Continued)

OTHER PUBLICATIONS

Written Opinion of the International Searching Authority issued in application PCT/JP2018/010096, completed Jun. 1, 2018 and mailed Jun. 12, 2018.

(Continued)

*Primary Examiner* — LaToya M Louis
(74) *Attorney, Agent, or Firm* — Merchant & Gould P.C.

(57) ABSTRACT

In some embodiments, a positive pressure exhale valve for a breathing apparatus that opens when internal pressure of a face piece of the breathing apparatus reaches a predetermined positive level includes a valve body, a first spring for always contacting the valve body so as to force the valve body in closing direction, and a braking body for opposing the valve body across a gap and contacting the valve body when a vibration body formed by the valve body and first spring experiences self-excited vibration, thereby suppressing the self-excited vibration.

11 Claims, 4 Drawing Sheets

(56) References Cited

U.S. PATENT DOCUMENTS

| | | | |
|---|---|---|---|
| 4,257,453 A | | 3/1981 | Kohnke |
| 4,481,974 A | * | 11/1984 | Schmitt ............... F16K 17/0433 |
| | | | 137/542 |
| 4,606,340 A | * | 8/1986 | Ansite .................... A62B 18/10 |
| | | | 251/63.4 |
| 4,693,270 A | * | 9/1987 | Yaindl .................... F16K 47/00 |
| | | | 137/513.3 |
| 4,870,963 A | | 10/1989 | Carter |
| 5,704,347 A | * | 1/1998 | Schlobohm ............ A62B 18/10 |
| | | | 128/205.24 |
| 8,573,248 B2 | * | 11/2013 | Mashak .............. A61M 16/208 |
| | | | 251/50 |
| 9,709,998 B2 | * | 7/2017 | Blanchard .......... G05D 16/0402 |
| 2012/0241025 A1 | * | 9/2012 | Chen .................. F16K 27/0236 |
| | | | 137/505 |

FOREIGN PATENT DOCUMENTS

| | | |
|---|---|---|
| JP | 5-337209 A | 12/1993 |
| JP | 2009-014153 A | 1/2009 |
| JP | 2014-161356 A | 9/2014 |
| KR | 10-2011-0026744 A | 3/2011 |

OTHER PUBLICATIONS

International Search Report issued in application PCT/JP2018/010096, completed Jun. 1, 2018 and mailed Jun. 12, 2018.

Office Action issued in related Japanese application 2017-081785 on Aug. 6, 2020.

Extended European Search Report issued in corresponding application 18788300.4, completed on Mar. 18, 2020 and mailed Mar. 26, 2020.

* cited by examiner

POSITIVE PRESSURE EXHALE VALVE FOR A BREATHING APPARATUS

This is a National Phase Application in the United States of International Patent Application No. PCT/JP2018/010096 filed Mar. 15, 2018, which claims priority on Japanese Patent Application No. 2017-081785, filed Apr. 18, 2017. The entire disclosures of the above patent applications are hereby incorporated by reference.

TECHNICAL FIELD

The present invention relates to a positive pressure exhale valve for a breathing apparatus that opens when internal pressure of a face piece of the breathing apparatus reaches predetermined positive level.

BACKGROUND ART

Patent Document No. 1 teaches a positive pressure exhale valve for a breathing apparatus that opens when internal pressure of a face piece of the breathing apparatus reaches predetermined positive level.

PRIOR ART DOCUMENT

Patent Document

Patent Document No. 1: Japanese Patent Laid-Open Publication No. 2014-161356

DISCLOSURE OF INVENTION

Problem to be Solved

A positive pressure exhale valve comprises a valve body and a spring for always contacting the valve body so as to force the valve body in closing direction. A vibration body formed by the valve body and spring may cause a problem if it experiences self-excited vibration for some reason. Once self-excited vibration starts, its amplitude increases over time to the point of generating abnormal noise that gives displeasure to a user of the breathing apparatus.

Therefore, an object of the present invention is to provide a positive pressure exhale valve for a breathing apparatus that opens when internal pressure of a face piece of the breathing apparatus reaches predetermined positive level, which positive pressure exhale valve comprising a valve body and a spring for always contacting the valve body so as to force the valve body in closing direction, and which positive pressure exhale valve is prevented from experiencing self-excited vibration of a vibration body formed by the valve body and spring.

Means for Achieving the Object

In accordance with the present invention, there is provided a positive pressure exhale valve for a breathing apparatus that opens when internal pressure of a face piece of the breathing apparatus reaches predetermined positive level, which positive pressure exhale valve comprising a valve body, a first spring for always contacting the valve body so as to force the valve body in closing direction, and a braking body for opposing the valve body across a gap and contacting the valve body when a vibration body formed by the valve body and first spring experiences self-excited vibration, thereby suppressing the self-excited vibration.

The positive pressure exhale valve does not open unless internal pressure of the face piece of the breathing apparatus reaches predetermined positive value, because it is always forced in closing direction by the first spring. So as not to interfere with operation of the positive pressure exhale valve, the braking body opposing the valve body across a gap does not contact the valve body during normal operation of the breathing apparatus. A problem can arise in which some kind of disturbance acting on the breathing apparatus or the vibration body formed by the valve body and first spring causes the vibration body to experience self-excited vibration. Once self-excited vibration starts, amplitude of the vibration grows larger over time and causes the valve body to contact the braking body. When the valve body contacts the braking body, braking force acts on the vibration body and stops the self-excited vibration, thereby stopping abnormal noise generated by the self-excited vibration.

In accordance with a preferred aspect of the present invention, the braking body is a columnar resilient body.

Use of the columnar resilient body simplifies structure of the positive pressure exhale valve, thereby decreasing production cost of the positive pressure exhale valve.

In accordance with a preferred aspect of the present invention, the braking body is a second spring.

Displacement of the valve body is restricted by the columnar resilient body because the columnar resilient body usually has spring constant much larger than that of the first spring. As a result, a disadvantage may arise wherein the valve body comes into contact with the braking body to be restricted in displacement to the point that divergence of the valve body appropriate for user breathing cannot be obtained when breathing of the user of the breathing apparatus is hard beyond normal level. The braking body made of a second spring provided with appropriate spring constant allows the valve body to displace farther after contacting the braking body, i.e., the second spring. As a result, self-excited vibration of the vibration body formed by the valve body and first spring can be suppressed and divergence of the valve body appropriate for user breathing can be obtained when breathing of the user of the breathing apparatus is hard beyond normal level.

In accordance with a preferred aspect of the present invention, spring constant of the second spring is set at a value larger than that of the first spring.

When spring constant of the second spring is set at a value larger than that of the first spring, braking force applied from the second spring to the vibration body formed by the valve body and first spring becomes large and the self-excited vibration of the vibration body can be effectively stopped.

In accordance with a preferred aspect of the present invention, the second spring is a coil spring whose one end distant from the valve body engages a hook formed on a support member and whose tip portion of said one end is bent and passed through a hole formed in the support member.

A coil spring is easily available and therefore a good choice for the second spring. When a coil spring is used for the second spring, it is necessary to engage one end of the coil spring distant from the valve body with a support member. It is effective to engage the coil spring with a hook formed on the support member at one end distant from the valve body. Said one end of the coil spring that engages the hook on the support member must be a flat portion. If a slanted portion of said one end of the coil spring should engage the hook on the support member, the coil spring would slant as a whole and cause one side of the coil spring to contact the valve body and thereby impair the coil spring's function of suppressing self-excited vibration. When a tip portion of said one end of the coil spring is bent and passed through a hole formed in the support member, relative circumferential position between the coil spring and the support member is fixed and the flat portion of said one end of the coil spring can surely engage the hook on the support member.

MODES FOR CARRYING OUT THE INVENTION

A positive pressure exhale valve for a breathing apparatus in accordance with a preferred embodiment of the present invention will be described.

Figure 1:
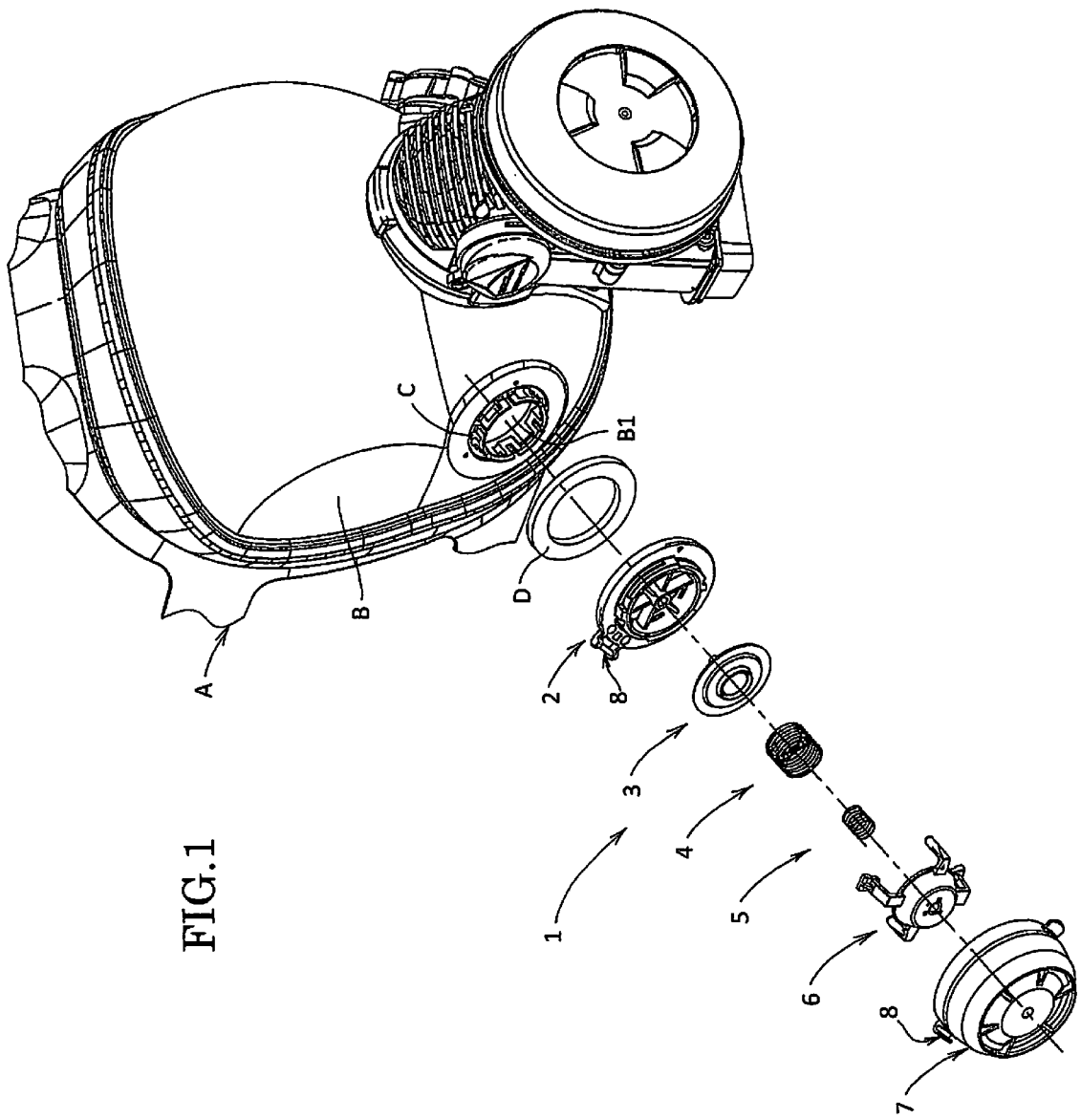
FIG. 1 is an exploded perspective view of a breathing apparatus provided with a positive pressure exhale valve in accordance with a preferred embodiment of the present invention.
Figure 2:
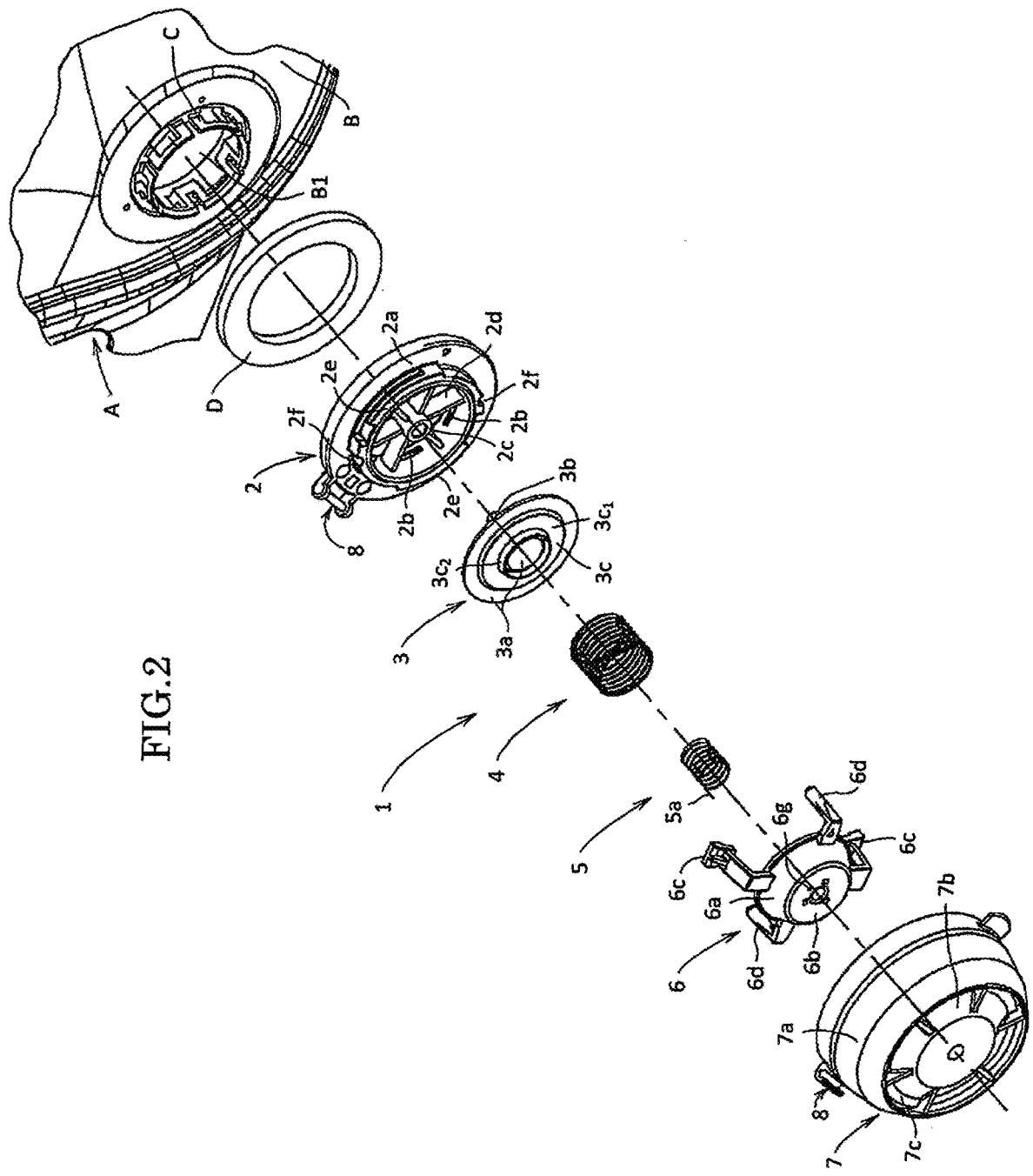
FIG. 2 is an exploded partial perspective view of a breathing apparatus provided with a positive pressure exhale valve in accordance with a preferred embodiment of the present invention.
Figure 3:
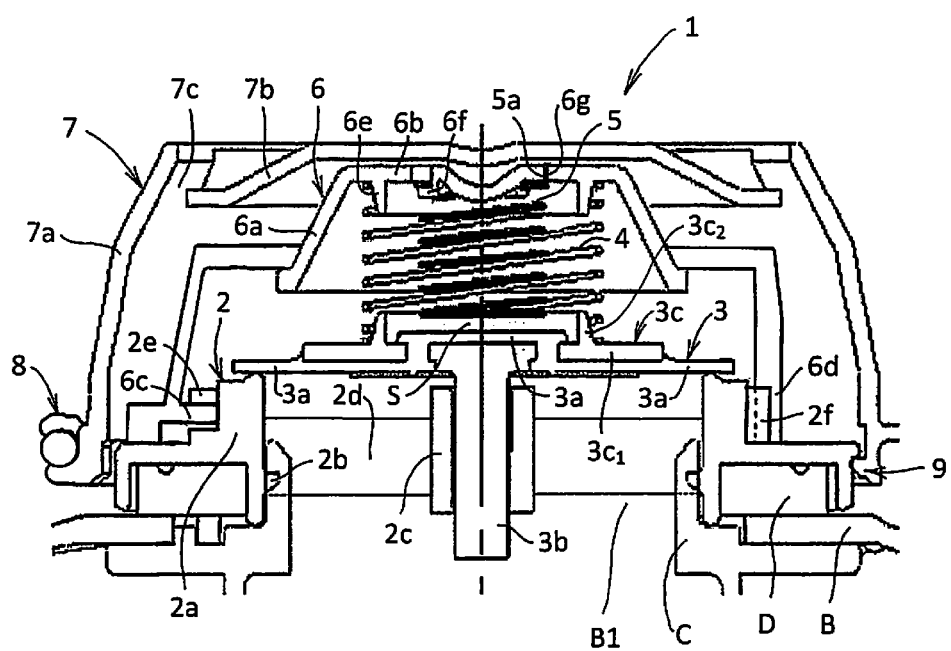
FIG. 3 is a sectional view of a positive pressure exhale valve in accordance with a preferred embodiment of the present invention.
Figure 4:
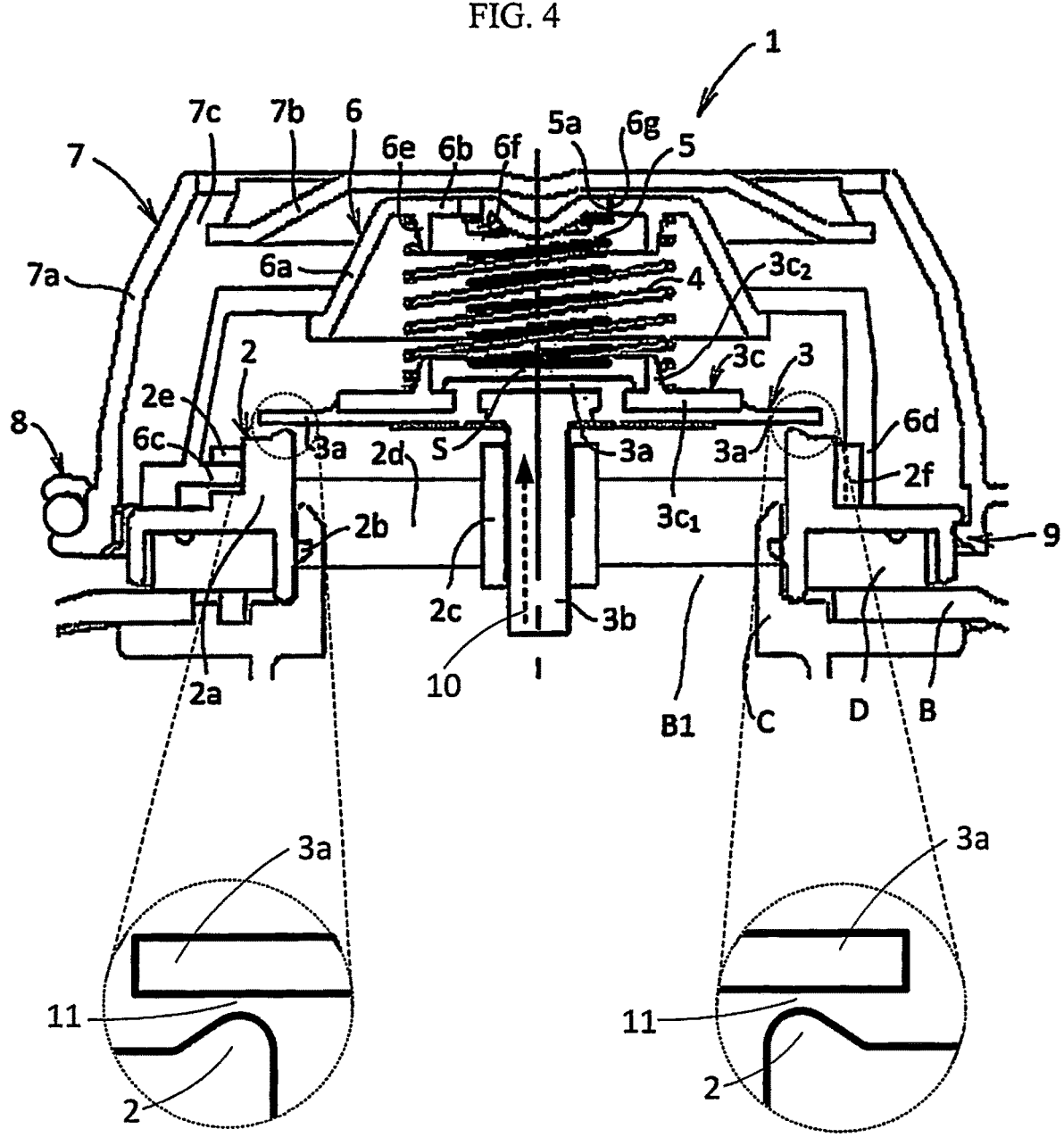

As shown in FIGS. 1 to 3, a breathing apparatus A is provided with a face piece B. The face piece B is provided with a circular opening B1 at one side portion. An annular shaped exhale valve receiving member C is passed through the opening B1 from the inside of the face piece B and fixed to the face piece B.

A positive pressure exhale valve 1 covers the opening B1 from the outside of the face piece B and is snap fitted on and fixed to the exhale valve receiving member C through an annular shaped seal member D.

The positive pressure exhale valve 1 is provided with an exhale valve seat 2. The exhale valve seat 2 is provided with an annular shaped valve seat forming member 2a and plurality of hooks 2b for snap fitting the valve seat forming member 2a on the exhale valve receiving member C. The hooks 2b are disposed circumferentially distanced from each other and formed on the valve seat forming member 2a. The positive pressure exhale valve 1 is further provided with a tubular bearing 2c located at the center of a circle formed by the valve seat forming member 2a and through which a valve shaft of a valve body that will be described later is inserted, a plurality of arm members 2d for connecting the tubular bearing 2c to the valve seat forming member 2a, a pair of hooks 2e of a female part of a bayonet connection mechanism, and a pair of recesses 2f of a female part of a lock mechanism.

The positive pressure exhale valve 1 is provided with a valve body 3. The valve body 3 is provided with a circular disk shaped flexible main valve body 3a made of silicon rubber, a valve shaft 3b made of hard plastic material and disposed coaxially with the main valve body 3a, and an annular shaped spring holder 3c made of hard plastic material and disposed coaxially with the main valve body 3a. The spring holder 3c is provided with an annular shaped plate portion $3c_1$ and a cylindrical portion $3c_2$ disposed at an inner peripheral portion of the annular shaped plate portion $3c_1$. The main valve body 3a, the valve shaft 3b and the spring holder 3c are insert molded integrally with each other.

The positive pressure exhale valve 1 is provided with a first coil spring 4. Opposite ends of the first coil spring 4 form a pair of flat planes extending at right angles to the longitudinal axis of the coil spring 4 and extending parallel with each other. The coil spring 4 fits on the cylindrical portion $3c_2$ of the spring holder 3c and abuts the annular plate portion $3c_1$ at one end.

The positive pressure exhale valve 1 is provided with a second coil spring 5 disposed coaxially with the first coil spring 4. The second coil spring 5 is formed smaller in diameter and shorter in length than the first coil spring 4. The second coil spring 5 is disposed inside of the first coil spring 4. Spring constant of the second coil spring 5 is set at larger than that of the first coil spring 4. The second coil spring 5 operates as a braking member for a vibration body formed by the valve body 3 and first coil spring 4. Opposite ends of the second coil spring 5 form a pair of flat planes extending at right angles to the longitudinal axis of the second coil spring 5 and extending parallel with each other. The second coil spring 5 opposes a portion of the main valve body 3a extending inside of the cylindrical portion $3c_2$ of the spring holder 3c across a predetermined gap at one end. Tip portion of the other end of the second coil spring 5 is bent in the extending direction of longitudinal axis of the second coil spring 5.

The positive pressure exhale valve 1 is provided with a spring retainer G. The spring retainer 6 is provided with a conical circumferential side wall 6a, a top wall 6b and a pair of hooks 6c of a male part of a bayonet connection mechanism. The hooks 6c are formed by tip portions of a pair of leg portions extending from the circumferential side wall 6a. The spring retainer 6 is further provided with a pair of hooks 6d of a male part of a lock mechanism. The hooks 6d are formed by tip portions of another pair of leg portions extending from the circumferential side wall 6a. The spring retainer 6 is further provided with a cylindrical portion 6e formed on back side of the top wall 6b, three second spring engaging hooks 6f disposed circumferentially distanced from each other and formed on back side of the top wall 6b, and a small diameter through hole 6g formed in the top wall 6b for use in positioning the second coil spring 5.

The hooks 2e of the female part and the hooks 6c of the male part can be detachably engaged with each other and form a bayonet connection mechanism for connecting a pair of members by pushing and twisting operation. The spring retainer 6 and the exhale valve seat 2 are detachably connected by the aforesaid bayonet connection mechanism. The hooks 6d of the male part and the recesses 2f of the female part can be detachably engaged with each other and form a lock mechanism. Connection between the spring retainer 6 and the exhale valve seat 2 is stably maintained by the aforesaid lock mechanism.

The other end of the first coil spring 4 fits on the cylindrical portion 6e on the back side of the top wall 6b of the spring retainer 6 and abuts the back side of the top wall 6b. The first coil spring 4 clamped at opposite ends by the valve body 3 and the spring retainer 6 forces the valve body 3 in closing direction so as to abut the main valve body 3a on the valve seat forming member 2a.

The second coil spring 5 is retained by the spring retainer 6 with the other end forming a flat plane engaged with the three hooks 6f on the back side of the top wall 6b and tip portion 5a of the other end passed through the small through hole 6g of the top wall 6b. As aforementioned, said one end of the second coil spring 5 opposes the portion of the main valve body 3a extending inside of the cylindrical portion $3c_2$ of the spring holder 3c across a predetermined gap. Said gap is determined based on measurements of displacement of the valve body 3 carried out on an actual positive pressure exhale valve 1 when the exhale valve 1 operates normally and when the exhale valve 1 experiences self-excited vibration.

The positive pressure exhale valve 1 is provided with a cover member 7. The cover member 7 is provided with a conical circumferential side wall 7a and a top plate 7b fixed to the circumferential side wall 7a through a plurality of arm members. An annular opening 7c is formed between the top plate 7b and the circumferential side wall 7a. The annular opening 7c is divided into a plurality of intermittent arc openings by said plurality of arm members.

The cover member 7 is connected to the exhale valve seat 2 to be capable of opening and closing through a hinge mechanism 8.

Closed condition of the cover member 7 is maintained to be releasable through a snap-fitting mechanism 9.

Operation of the positive pressure exhale valve 1 will be described.

The breathing apparatus A is provided with a motor fan. In the breathing apparatus A, internal pressure of the face piece B is always maintained positive and external air is supplied to the face piece B through the motor fan only when a user of the breathing apparatus inhales.

When the internal pressure of the face piece B reaches a predetermined level during exhale of the user, the valve body 3 moves in opening direction against biasing force of the first coil spring 4 so as to open the positive pressure exhale valve 1. As a result, exhaled air in the face piece B is discharged to the external environment.

When the breathing apparatus A is used normally and breathing of the user is not abnormally hard, the valve body 3 does not contact the second coil spring 5 during exhale, so that the valve body 3 opens and closes under the biasing forces from the first coil spring 4 and the internal pressure of the face piece B.

A problem can happen in which some kind of external disturbance acts on the breathing apparatus A or a vibration body formed by the valve body 3 and first coil spring 4 so that the vibration body experiences self-excited vibration. Once the self-excited vibration starts, its amplitude grows larger over time to the point of generating abnormal noise that gives displeasure to a user of the breathing apparatus A. However, in the breathing apparatus A, when the amplitude of the self-excited vibration of the vibration body formed by the valve body 3 and first coil spring 4 becomes large, the valve body 3 contacts the second coil spring 5, i.e., a braking body. When the valve body 3 contacts the second coil spring 5, braking force acts on the vibration body 3 from the second coil spring 5 so as to stop the self-excited vibration, thereby stopping abnormal noise generated by the self-excited vibration. As can be seen from the above explanation, self-excited vibration of the vibration body formed by the valve body 3 and first coil spring 4 is effectively suppressed in the positive pressure exhale valve 1.

The second coil spring 5 has an advantage in that since it does not contact the valve body 3 during normal operation of the positive pressure exhale valve 1, it does not interfere with normal operation of the positive pressure exhale valve 1 and therefore does not obstruct normal operation of the positive pressure exhale valve 1.

Spring constant of the second coil spring 5 is set at a value larger than that of the first coil spring 4 so that large braking force is applied from the second coil spring 5 to the vibration body formed by the valve body 3 and first coil spring 4. Thus, the self-excited vibration of the vibration body can be effectively stopped.

Spring constant of the second coil spring 5 is desirably set at an appropriate value that enables the valve body 3 to continue to displace in opening direction after it contacts the second coil spring 5. This makes it possible not only to suppress the self-excited vibration of the vibration body formed by the valve body 3 and first coil spring 4 but also to increase divergence of the positive pressure exhale valve 1 to a level appropriate for user breathing when the breathing of the user of the breathing apparatus A is extremely hard.

As the second coil spring 5 is easily available, it is suitable for use as a braking member for the vibration body formed by the valve body 3 and first coil spring 4. When the second coil spring 5 is used as a braking member, it is necessary to retain the second coil spring 5 by the spring retainer 6 at said another end distant from the valve body 3. An effective retaining method is to engage the second coil spring 5 with the hooks 6f formed on the spring retainer 6 at said another end distant from the valve body 3. A flat portion of said another end of the second coil spring 5 must engage the hooks 6f of the spring retainer G. If a slanted portion of said another end of the second coil spring 5 should engage the hooks 6f of the spring retainer 6, the second coil spring 5 would slant as a whole and cause one side of the second coil spring 5 to contact the valve body 3 and thereby impair the coil spring's function of suppressing self-excited vibration. When a tip portion of said another end of the second coil spring 5 is bent and passed through the hole 6g formed in the spring retainer 6, relative circumferential position between the second coil spring 5 and the spring retainer 6 is fixed and the flat portion of said another end of the second coil spring 5 can surely engage the hooks 6f of the spring retainer G.

Instead of the second coil spring 5, a hard or soft columnar resilient body can be used as the braking member for the vibration body formed by the valve body 3 and first coil spring 4. The columnar resilient body simplifies structure of the positive pressure exhale valve 1, thereby decreasing production cost of the positive pressure exhale valve 1. However, once the valve body 3 contacts the columnar resilient body, displacement of the valve body 3 is restricted by the columnar resilient body because the columnar resilient body usually has spring constant much larger than that of the first coil spring 4. As a result, a disadvantage may arise wherein the valve body 3 comes into contact with the columnar resilient body to be restricted in displacement to the point that divergence of the valve body 3 appropriate for user breathing cannot be obtained when breathing of the user of the breathing apparatus 1 is hard beyond normal level.

INDUSTRIAL APPLICABILITY

The present invention can be widely used for positive pressure exhale valves for breathing apparatuses

BRIEF DESCRIPTION OF THE REFERENCE NUMERALS

A Breathing apparatus
B Face piece
C Exhale valve receiving member
D Seal member
1 Positive pressure exhale valve
2 Exhale valve seat
3 Valve body
4 First coil spring 5 Second coil spring
6 Spring retainer
7 Cover member

The invention claimed is:

1. A positive pressure exhale valve for a breathing apparatus that opens when internal pressure of a face piece of the breathing apparatus reaches predetermined positive level, which pressure exhale valve comprising a valve body, a valve seat opposing the valve body with a space between the valve seat and the valve body, a first spring for always contacting the valve body so as to force the valve body in a closing direction, and a braking body opposing the valve seat with the valve body between the braking body and the valve seat, the braking body opposing the valve body across a gap from a direction opposite the closing direction so that the braking body does not always contact the valve body and the braking body contacting the valve body when a vibration body formed by the valve body and the first spring experiences self-excited vibration, thereby suppressing the self-excited vibration.

2. A positive pressure exhale valve of claim 1, wherein the braking body is a columnar resilient body.

3. A positive pressure exhale valve of claim 1, wherein the braking body is a second spring.

4. A positive pressure exhale valve of claim 3, wherein the second spring is provided with spring constant larger than that of the first spring.

5. A positive pressure exhale of claim 4, wherein the second spring is a coil spring whose one end distant from the valve body engages a hook formed on a support member and whose tip portion of said one end is bent and passed through a hole formed in the support member.

6. A positive pressure exhale valve of claim 3, wherein the second spring is a coil spring whose one end distant from the valve body engages a hook formed on a support member and whose tip portion of said one end is bent and passed through a hole formed in the support member.

7. A positive pressure exhale valve of claim 1, wherein:
the gap is a predetermined gap; and
the valve body is displaceable in toward the braking body when the internal pressure of the face piece of the breathing apparatus reaches the predetermined positive level.

8. A positive pressure exhale valve of claim 7, wherein the valve body comprises a flexible main valve body.

9. A positive pressure exhale valve for a breathing apparatus that opens when internal pressure of a face piece of the breathing apparatus reaches predetermined positive level, which pressure exhale valve comprising a valve body, a valve seat opposing the valve body with a space between the valve seat and the valve body, a first spring for always contacting the valve body so as to force the valve body in a closing direction, and a braking body comprising a second spring and opposing the valve seat with the valve body between the braking body and the valve seat, the braking body opposing the valve body across a gap from a direction opposite the closing direction so that the braking body does not always contact the valve body and the braking body contacting the valve body when a vibration body formed by the valve body and the first spring experiences self-excited vibration, thereby suppressing the self-excited vibration, wherein the second spring is provided with spring constant larger than that of the first spring.

10. A positive pressure exhale of claim 9, wherein the second spring is a coil spring whose one end distant from the valve body engages a hook formed on a support member and whose tip portion of said one end is bent and passed through a hole formed in the support member.

11. A positive pressure exhale valve for a breathing apparatus that opens when internal pressure of a face piece of the breathing apparatus reaches predetermined positive level, which pressure exhale valve comprising a valve body, a valve seat opposing the valve body with a space between the valve seat and the valve body, a first spring for always contacting the valve body so as to force the valve body in a closing direction, and a braking body comprising a second spring and opposing the valve seat with the valve body between the braking body and the valve seat, the braking body opposing the valve body across a gap from a direction opposite the closing direction so that the braking body does not always contact the valve body and the braking body contacting the valve body when a vibration body formed by the valve body and the first spring experiences self-excited vibration, thereby suppressing the self-excited vibration, wherein the second spring is a coil spring whose one end distant from the valve body engages a hook formed on a support member and whose tip portion of said one end is bent and passed through a hole formed in the support member.

* * * * *